United States Patent [19]

Vora et al.

[11] Patent Number: 5,599,955
[45] Date of Patent: Feb. 4, 1997

[54] PROCESS FOR PRODUCING PROPYLENE OXIDE

[75] Inventors: Bipin V. Vora, Darien; Peter R. Pujado, Palatine, both of Ill.

[73] Assignee: UOP, Des Plaines, Ill.

[21] Appl. No.: 605,602

[22] Filed: Feb. 22, 1996

[51] Int. Cl.$^6$ .................. C07D 301/14; C07D 301/16
[52] U.S. Cl. ............................ 549/525; 549/526
[58] Field of Search ...................... 549/525, 526

[56] References Cited

U.S. PATENT DOCUMENTS

| | | | |
|---|---|---|---|
| 3,928,483 | 12/1975 | Chang et al. | 260/668 |
| 4,025,575 | 5/1977 | Chang et al. | 260/682 |
| 4,052,479 | 10/1977 | Chang et al. | 260/682 |
| 4,447,669 | 5/1984 | Hamon et al. | 585/640 |
| 4,496,786 | 1/1985 | Santilli et al. | 585/640 |
| 4,499,314 | 2/1985 | Seddon et al. | 585/408 |
| 4,547,616 | 10/1985 | Avidan et al. | 585/640 |
| 4,677,242 | 6/1987 | Kaiser | 585/638 |
| 4,677,243 | 6/1987 | Kaiser | 585/638 |
| 4,843,183 | 6/1989 | Inui | 585/640 |
| 4,861,938 | 8/1989 | Lewis et al. | 585/640 |
| 4,973,792 | 11/1990 | Lewis et al. | 585/638 |
| 5,095,163 | 3/1992 | Barger | 585/640 |
| 5,191,141 | 3/1993 | Barger et al. | 585/640 |

*Primary Examiner*—Amelia Owens
*Attorney, Agent, or Firm*—Thomas K. McBride; John G. Tolomei; Richard P. Silverman

[57] ABSTRACT

The present invention provides an integrated process for the production of propylene oxide from an alternate feedstream such as synthesis gas. In the process, propylene oxide is produced from a feedstream comprising hydrogen and a carbon oxide. A portion of the feedstream is passed to an oxygenate production zone to produce an oxygenate stream comprising methanol and dimethyl ether, and the oxygenate stream is passed to an olefin production zone containing a metal aluminophosphate catalyst to produce a propylene stream. The propylene stream is epoxidized with hydrogen peroxide which has been produced from hydrogen separated from a portion of the feedstream. The spent water stream produced by the epoxidation reaction is treated to remove heavy components and returned to the hydrogen peroxide production zone. The return of the unreacted propylene from the epoxidation reaction zone for its subsequent recovery and recycle permits a less complicated, lower energy propylene separation. The recycling of spent water from the epoxidation reaction zone and the removal of heavy compounds eliminates a low value water stream and the recovery of heavy hydrocarbons therefrom produces a valuable secondary product.

21 Claims, 2 Drawing Sheets

PROCESS FOR PRODUCING PROPYLENE OXIDE

FIELD OF THE INVENTION

This invention relates to a process for the production of propylene oxide from a synthesis gas feedstream.

BACKGROUND OF THE INVENTION

Propylene oxide is a significant organic chemical product. Propylene oxide is produced world wide in large volumes as an organic intermediate. The most important use for propylene oxide is in the production of polyether polyols, a feedstock for polyurethane manufacture. Polyurethanes are used in the production of flexible and rigid foam, microcellular applications, and coatings used in industries ranging from automobiles to construction. Propylene oxide is also used as a raw material for the production of propylene glycols, surfactants, glycol ethers and other specialty organic compounds.

Propylene is a light olefinic hydrocarbon. Light olefins have traditionally been produced through the process of steam or catalytic cracking. Because of the limited availability and high cost of petroleum sources, the cost of producing light olefins from such petroleum sources has been steadily increasing. Light olefins serve as feeds for the production of numerous chemicals. As the emerging economies of various countries strain toward growth and expansion, the demand for light olefins will increase dramatically. The search for alternative materials for light olefin production has led to the use of oxygenates such as alcohols, and more particularly to the use of methanol, ethanol, and higher alcohols or their derivatives. These alcohols may be produced by fermentation or from synthesis gas. Synthesis gas can be produced from natural gas, petroleum liquids, and carbonaceous materials including coal, wood, recycled plastics, municipal wastes, or any organic material. Thus, alcohol and alcohol derivatives may provide non-petroleum based routes for the production of olefin and other key building block hydrocarbons like propylene oxide.

Molecular sieves such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. Nos. 3,928,483, 4,025,575, 4,052,479 (Chang et al.); U.S. Pat. No. 4,496,786 (Santilli et al.); U.S. Pat. No. 4,547,616 (Avidan et al.); U.S. Pat. No. 4,677,243 (Kaiser); U.S. Pat. No. 4,843,183 (Inui); U.S. Pat. No. 4,499,314 (Seddon et al.); U.S. Pat. No. 4,447,669 (Harmon et al.); U.S. Pat. No. 5,095,163 (Barger); U.S. Pat. No. 5,191,141 (Barger); U.S. Pat. No. 5,126,308 (Barger); U.S. Pat. No. 4,973,792 (Howard); and U.S. Pat. No. 4,861,938 (Lewis). The process for the production of olefins from oxygenates may be generally conducted in the presence of one or more diluents which may be present in the oxygenate feed in an amount between about 1 and about 99 molar percent, based on the total number of moles of all feed and diluent components fed to the reaction zone (or catalyst). Diluents include—but are not limited to—helium, argon, nitrogen, carbon monoxide, carbon dioxide, hydrogen, water, paraffins, hydrocarbons (such as methane and the like), aromatic compounds, or mixtures thereof. U.S. Pat. Nos. 4,861,938 and 4,677,242 particularly emphasize the use of a diluent combined with the feed to the reaction zone to maintain sufficient catalyst selectivity toward the production of light olefin products, particularly ethylene.

The predominant process for the production of propylene oxide is the chlorohydrin process. In the chlorohydrin process, a hypochlorous acid is added to propylene which produces a propylene chlorohydrin intermediate and the intermediate is subsequently hydrolyzed with a base to yield propylene oxide. At one time, lime was used as the base in the dehydrochorination reaction which resulted in the production of calcium chloride. Environmental concern over the disposal of dilute calcium chloride solutions led to the use of caustic soda. The chlorohydrin press is generally integrated with a chlor-alkali plant to provide the chlorine and provide a use for the dilute salt stream.

Another technology for the production of propylene oxide comprises the epoxidation of propylene by an organic hydroperoxide which yields an alcohol as a co-product. Organic hydroperoxides typically employed in the epoxidation of propylene include t-butyl hydroperoxide and ethylbenzene hydroperoxide. These organic hydroperoxides epoxidize propylene in the presence of a soluble metal compound such as molybdenum, vanadium, tungsten, and titanium in solution as the epoxidation catalyst. When isobutane is the starting material, the co-product alcohol is t-butyl alcohol which is used in gasoline manufacture. When ethylbenzene is used, the alcohol produced is 1-phenyl ethanol, which is subsequently dehydrated to styrene.

Thus, processes for the production of propylene oxide generally require significant integration with associated intermediate steps in the production of the propylene oxide to avoid the production of low value process streams or must be combined with the production of other major products such as gasoline or styrene. Processes are sought which produce propylene oxide from alternative materials such as non-petroleum based materials. Processes for the production of propylene oxide are sought which minimize or eliminate the production of low value waste streams and produce a minimum of co-products.

SUMMARY OF THE INVENTION

The present invention provides a process for the production of propylene oxide from an alternative feedstream such as synthesis gas that is integrated with a process for the production of light olefins comprising propylene and the epoxidation of propylene with hydrogen peroxide. The integrated processing scheme provides hydrogen for the production of the hydrogen peroxide and water for the recovery of the hydrogen peroxide by using the water recovered from the epoxidation reaction. The integrated scheme provides a process for the production of propylene oxide which does not require the environmental complexities of operating a chlorine plant or the co-production of secondary products, which significantly lowers overall costs by simplifying the complex and removing the dependence of the profitability of the complex on major co-products. The return of the unreacted propylene from the epoxidation reaction zone for its recovery and recycle permits a less complex and lower energy separation of the propylene following the production of the light olefins.

The invention provides a process for the production of propylene oxide from a feedstream comprising hydrogen and a carbon oxide. The process comprises passing a portion of the feedstream to an oxygenate production zone to produce an oxygenate and passing the oxygenate to an olefin production zone containing a metal aluminophosphate catalyst to produce a light hydrocarbon stream comprising propylene. A crude propylene stream is separated from the light hydrocarbon stream and the crude propylene stream is passed with an aqueous hydrogen peroxide stream to an epoxidation reaction zone containing a epoxidation catalyst to produce a propylene oxide product, a light ends stream, and a spent water stream. The light ends stream comprises unreacted propylene and the spent water stream comprises heavy components. A portion of the feedstream is separated in a hydrogen separation zone to provide a hydrogen stream comprising hydrogen, and the hydrogen stream and an oxygen-containing stream are reacted in a peroxide production zone to produce hydrogen peroxide and the hydrogen peroxide is removed with a water stream to produce the aqueous hydrogen peroxide stream. The spent water stream is treated to remove the heavy hydrocarbons providing a treated water stream, and at least a portion of the treated water stream is recycled to provide the water stream. In another embodiment, at least a portion of the light ends stream is returned to be admixed with the light hydrocarbon stream to recover the unreacted propylene.

DETAILED DESCRIPTION OF THE INVENTION

Figure 1:
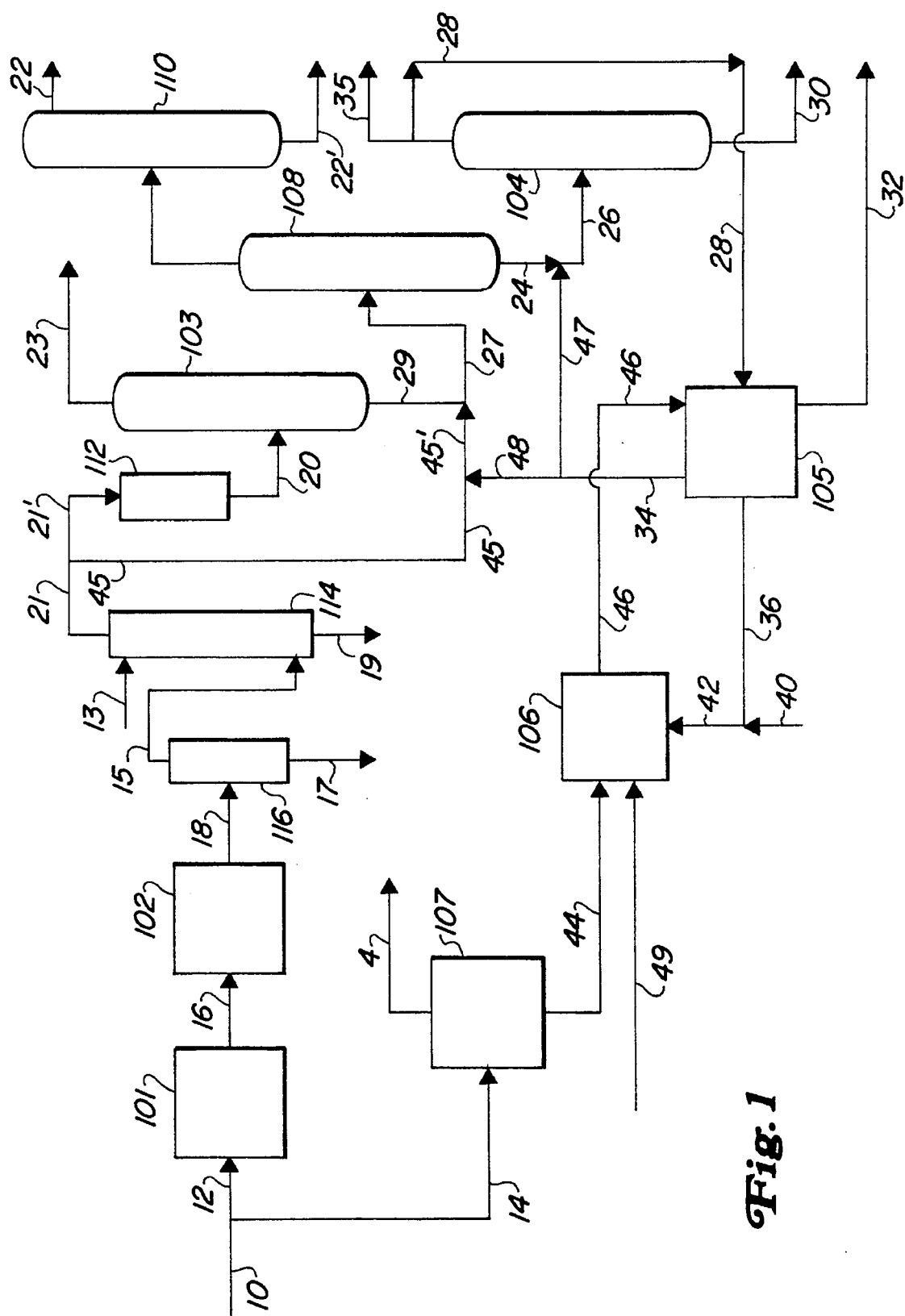
FIG. 1 is a schematic process flow diagram illustrating the process of the instant invention integrating an epoxidation process with the production of propylene from oxygenates.

The present invention provides an integrated processing scheme for the production of propylene oxide from a feedstream comprising hydrogen and a carbon oxide such as carbon monoxide or carbon dioxide. The feedstream as employed in the present invention provides both the basis for the production of propylene and the source of hydrogen for the production of hydrogen peroxide. The feedstream, preferably derived from a synthesis gas generation plant, comprises hydrogen and carbon oxides such as carbon monoxide and carbon dioxide. The feedstream will comprise a molar ratio of hydrogen to carbon oxide of between about 2 and about 3.5. According to the present invention, a portion of the feedstream is passed to a hydrogen separation zone to obtain a hydrogen stream having a purity of greater than about 80 vol-% and a gas waste stream enriched in carbon oxide relative to the feedstream. Preferably the purity of the hydrogen stream is greater than about 99.9 vol-%. The hydrogen separation from the carbon oxide may be performed by any well-known, suitable method including pressure swing adsorption, cryogenic fractionation, membrane separation, and combinations thereof, an example of which is disclosed in U.S. Pat. No. 4,863,492 which is hereby incorporated by reference. Of these methods, hydrogen separation using a permeable membrane is preferred. The gas waste stream, enriched in the carbon oxide by the hydrogen separation zone is returned to an upstream synthesis gas plant or is admixed with the portion of the feedstream passed to an oxygenate formation zone.

With respect to the preferred method for the production of hydrogen, a portion of the feedstream at a temperature of about −30° to about 120° C. and a pressure ranging from about 700 kPa to about 13.8 MPa is passed to a membrane separation zone. Permeable membrane systems suitable for use in the practice of the invention are available in the art. Such permeable membranes are capable of selectively permeating a component such as hydrogen in the feedstream generally at relatively high pressures, e.g., pressures typically in excess of about 1700 kPa (about 250 psia), commonly up to about 7,000 kPa (about 1,000 psia) or higher. Inlet means are provided for passing a feedstream at the desired pressure to the feed inlet portion of the separator, with outlet means being provided for withdrawing the key component rich permeate gas from the separator at a reduced pressure. Other outlet means are provided for separately withdrawing the non-permeate portion of the gas stream, i.e., the portion not passing through the membrane, from the separator, essentially at the feedstream pressure. In commercially available embodiments, the permeable membrane is commonly in the form of either spiral wound or hollow fibers, made of cellulose acetate, cellulose triacetate, polysulfone material or any other suitable material, assembled within the separator structure. Such fibers may be assembled into compact bundles to provide a large membrane area available for the passage of the desired product gas therethrough. Using hollow fibers, the feed inlet portion of the separator and the non-permeate gas outlet means are conveniently in fluid communication within the separator on the outside of such hollow fibers. The permeate gas outlet means are then in fluid communication with the inside of the hollow fibers. In practical convenient embodiments, the non-permeate gas outlet means and the permeate gas outlet means are at opposite ends of the separator, with the feed inlet means being positioned near the permeate gas outlet means. In operation, the pressurized feed gas enters the separator and hydrogen or other key component in the feed gas selectively permeates the membrane walls. The key component rich permeate gas passes through the interior of the membrane bores at reduced pressure and is delivered to the outlet means at one end of the separator, while non-permeate gas passes to the outlet means typically positioned at the opposite end of the separator. The permeate stream, withdrawn from the membrane separation zone comprises hydrogen. Preferably, the permeate stream comprises more than about 80 mol-% hydrogen, and more preferably, the permeate stream comprises from about 95 to about 99.9 mol-% hydrogen. In those cases in which carbon dioxide is present in the synthesis gas and the carbon dioxide permeates with the hydrogen, additional means for removal of carbon dioxide can be provided to raise the hydrogen purity of the permeate stream to the desired level.

A synthesis gas stream is typically derived from a syngas production zone or synthesis gas plant to convert petroleum, natural gas, coal, or wood into a synthesis gas comprising hydrogen and a carbon oxide. A synthesis gas plant, for example, based on steam reforming of light hydrocarbons, conventionally operates at a reaction temperature ranging from about 600° C.–950° C., a pressure ranging from about 10–30 bar, and a water to carbon molar ratio ranging from about 2.0 to about 3.5. Impurities such as sulfur compounds, nitrogen compounds, particulate matter, and condensibles are removed in the conventional manner to provide the synthesis gas stream reduced in contaminants and containing a molar ratio of hydrogen to carbon oxide (carbon monoxide plus carbon dioxide) ranging from about 2 to about 3, and more typically the molar ratio of hydrogen to carbon oxide varies from about 2.0 to about 2.3 which is suitable as a feed to the carbon oxide conversion zone.

According to the present invention, at least a portion of a synthesis gas stream is passed to a carbon oxide conversion zone. In the carbon oxide conversion zone, the synthesis gas undergoes conversion to form reduction products of carbon oxides, such as alcohols, at conditions including a reactor temperature ranging from about 150° C. (300° F.) to about 450° C. (850° F.) at a pressure ranging from about 1 to about 1000 atmospheres over a variety of catalysts, including: CuO/ZnO/Al$_2$O$_3$, CuO/ZnO/Cr$_2$O$_3$, ZnO/Cr$_2$O$_3$, Fe, Co, Ni, Ru, Os, Pt, and Pal. Catalysts based on ZnO for the production of methanol and dimethyl ether are preferred. An oxygenate product stream comprising methanol and/or dimethyl ether is withdrawn from the carbon oxide conversion zone.

At least a portion of the oxygenate product is passed to an olefin production zone to produce a reactor effluent comprising light olefins having from 2 to 4 carbon atoms per molecule and water. The olefin production zone is maintained at a reaction temperature ranging from about 350° C. to about 525° C. and a pressure of about 1 to about 5 atmospheres. The olefin production zone contains a molecular sieve catalyst, and preferably contains a metal aluminophosphate catalyst such as a SAPO catalyst for the conversion of at least a portion of the oxygenate product stream into C$_2$–C$_4$ olefins. The hydrocarbons produced in the olefin production zone include ethylene, propylene, and butylenes. In producing the hydrocarbons from oxygenates a water byproduct stream is also produced. Preferably, the olefin production zone contains a metal aluminophosphate catalyst selected from the group consisting of SAPO-34, SAPO-17, SAPO-18, and mixtures thereof, the catalyst being described in U.S. Pat. Nos. 4,440,871, 5,126,308, and 5,191,141 and hereby incorporated by reference.

A portion of the feedstream is passed to an oxygenate formation zone to produce an oxygenate stream which comprises alcohols, ethers, and mixtures thereof such as methanol, ethanol, propanol, dimethyl ether, and mixtures thereof. The oxygenate stream is passed to an olefin production zone wherein the oxygenate stream is contacted with a silicoaluminophosphate molecular sieve at effective process conditions to produce light olefins. Silicoaluminophosphate molecular sieves which produce light olefins are generally employable in the instant process. The preferred silicoaluminophosphates are those described in U.S. Pat. No. 4,440,871. The oxygenate stream is catalytically converted to hydrocarbons containing aliphatic moieties such as—but not limited to—methane, ethane, ethylene, propane, propylene, butylene, and limited amounts of other higher aliphatics. The total charge of the oxygenate stream to the olefin production zone may contain additional compounds such as diluents. A diluent is required to maintain the selectivity of the catalyst to produce light olefins, particularly ethylene and propylene. Examples of diluents which may be used are helium, argon, nitrogen, carbon monoxide, carbon dioxide, hydrogen, steam, paraffinic hydrocarbons, (e.g., methane), aromatic hydrocarbons, (e.g., benzene, toluene), and mixtures thereof. The amount of diluent used can vary considerably and is usually from about 5 to about 90 mole percent of the feedstock and preferably from about 15 to about 50 mole percent.

The oxygenate conversion process of the present invention is preferably conducted in the vapor phase such that the oxygenate feedstock is contacted in a vapor phase in a reaction zone with a molecular sieve catalyst at effective process conditions to produce hydrocarbons, i.e., an effective temperature, pressure, WHSV and, optionally, an effective amount of diluent, correlated to produce light olefins. The process is carried out for a period of time sufficient to produce the desired light olefin products. In general, the residence time employed to produce the desired product can vary from seconds to a number of hours. The oxygenate conversion process is effectively carried out over a wide range of pressures, including autogenous pressures. At pressures between about 0.001 atmospheres (0.76 torr) and about 1000 atmospheres (760,000 torr), the formation of light olefin products will be effected although the optimum amount of product will not necessarily form at all pressures. The preferred pressure is between about 0.01 atmospheres (7.6 torr) and about 100 atmospheres (76,000 torr). More preferably, the pressure will range from about 1 to about 10 atmospheres. The pressures referred to herein for the process are exclusive of the inert diluent, if any, that is present and refer to the partial pressure of the feedstock as it relates to oxygenate compounds and/or mixtures thereof. The temperature which may be employed in the oxygenate conversion process may vary over a wide range depending, at least in part, on the selected molecular sieve catalyst. In general, the process can be conducted at an effective temperature between about 200° C. (392° F.) and about 700° C. (1292° F.)

In the oxygenate conversion process wherein aliphatic hetero compounds are converted into light olefins, it is preferred that the catalysts have relatively small pores. The preferred small pore catalysts are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the catalyst and adsorption of the adsorbate is over three percent by weight of the adsorbate based on the weight of the catalyst. Certain of the catalysts useful in the present invention have pores with an average effective diameter of less than 5 Angstroms. The average effective diameter of the pores of preferred catalysts is determined by measurements described in D. W. Breck, *ZEOLITE MOLECULAR SIEVES* by John Wiley & Sons, New York (1974), hereby incorporated by reference in its entirety. The term effective diameter is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore.

Non-zeolitic molecular sieves suitable for use as a catalyst in the present invention include molecular sieves which have the proper effective pore size and are embraced by an empirical chemical composition, on an anhydrous basis, expressed by the empirical formula:

$$(EL_xAl_yP_z)O_2$$

where EL is a metal selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of metals, x represents the total amount of the metal mixture present. Preferred metals (EL) are silicon, magnesium and cobalt with silicon being especially preferred.

The preparation of various ELAPOs are well known in the art and may be found in U.S. Pat. No. 5,191,141 (ELAPO); U.S. Pat. No. 4,554,143 (FeAPO); U.S. Pat. No. 4,440,871 (SAPO); U.S. Pat. No. 4,853,197 (MAPO, MnAPO, ZnAPO, CoAPO); U.S. Pat. No. 4,793,984 (CAPO), U.S. Pat. No. 4,752,651 and U.S. Pat. No. 4,310,440 all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

A preferred embodiment of the invention is one in which the metal (EL) content varies from about 0.005 to about 0.05 mole fraction. If EL is more than one metal, then the total concentration of all the metals is between about 0.005 and 0.05 mole fraction. An especially preferred embodiment is one in which EL is silicon (usually referred to as SAPO). The SAPOs which can be used in the instant invention are any of those described in U.S. Pat. Nos. 4,440,871; 5,126,308, and 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å. Other SAPO, such as SAPO-17, as exemplified in Examples 25 and 26 of the '871 patent, and SAPO 18, as disclosed in WO95-05342 A1, are also preferred. The above patents are hereby incorporated by reference. The SAPO-17 structure is characterized in that it adsorbs oxygen, hexane, and water but does not adsorb isobutane, indicating that it has a pore opening of greater than about 4.3 Å and less than about 5.0 Å.

The preferred oxygenate conversion catalyst may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength, and the like to the solid particles. Filler and binder materials include, for example, synthetic and naturally occurring substances such as metal oxides, clays, silicas, aluminas, silica-aluminas, silicamagnesias, silica-zirconias, silica-thorias, silica-berylias, silica-titanias, silica-alumina-thorias, silica-alumina-zirconias, aluminophosphates, mixtures of these and the like. If matrix materials, e.g., binder and/or filler materials, are included in the catalyst composition, the non-zeolitic and/or zeolitic molecular sieves preferably comprise about 1% to 99%, more preferably about 5% to about 90% and still more preferably about 10% to about 80%, by weight of the total composition. The preparation of solid particles comprising catalyst and matrix materials is conventional and well known in the art and, therefore, need not be discussed in detail herein.

During the oxygenate conversion reaction, a carbonaceous material, i.e., coke is deposited on the catalyst. The carbonaceous deposit material has the effect of reducing the number of active sites on the catalyst which thereby affects the extent of the conversion. During the conversion process a portion of the coked catalyst is withdrawn from the reaction zone and regenerated to remove at least a portion of the carbonaceous material and returned to the oxygenate conversion reaction zone. Depending upon the particular catalyst and conversion, it can be desirable to substantially remove the carbonaceous material e.g., to less than 1 wt %, or only partially regenerate the catalyst, e.g., to from about 2 to 30 wt % carbon. Preferably, the regenerated catalyst will contain about 0 to 20% and more preferably from about 0 to 10% carbon. Additionally, during regeneration there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration. The details concerning the conditions for regeneration are known to those skilled in the art and need to be further disclosed herein.

Propylene from the olefin production zone is converted to produce propylene oxide in an epoxidation zone. In the propylene oxide zone, an aqueous hydrogen peroxide stream is reacted with a propylene containing stream over a metal-substituted silicate catalyst, wherein the metal is selected from the group consisting of molybdenum, cobalt, tungsten, chromium, titanium, and combinations thereof and preferably wherein the metal-substituted silicate is supported on titania at modest temperatures to produce the propylene oxide product, a spent water stream and an unreacted propylene stream. The epoxidation reaction temperature ranges between about 0° C. and about 100° C. The epoxidation reaction may be conducted at atmospheric pressure or elevated pressures to increase solubility of the gaseous reactants in the reaction medium. For example, increased pressure increases propylene solubility in aqueous solution with an increase in overall rate of propylene epoxide formation, and preferably the propylene solubility is increased by using a reaction medium such as a suitable solvent in which the various reactants are mutually soluble. Such suitable solvents are well-known in the art and may be selected, but not limited to the group consisting of alcohols, ethers, ketones and other similar polar materials. Preferably the epoxidation reaction is carried out at a pressure less than about 7 MPa (1000 psig), and more preferably the epoxidation reaction is carried out at a pressure less than about 3.5 MPa (500 psig). The hydrogen peroxide may be present in the aqueous hydrogen peroxide stream 46 at a concentration as low as about 2 weight percent and as high as about 50 weight percent. It is preferable that the propylene be present in molar excess, perhaps as much as 2–10 moles per mole of hydrogen peroxide. In general, the ratio of propylene to hydrogen peroxide may range from 1:10 to 10:1. The epoxidation reactor may employ any of the conventional process techniques such as a fixed bed, a continuous stirred tank reactor, a radial bed process and so on. In such cases, the metal-substituted silicate catalyst, such as titania-supported titanosilicate as described in U.S. Pat. Nos. 5,354,875 and 4,833,260 and hereby incorporated by reference, may be used as pellets, extrudates, spheres, and the like. Further, the epoxidation catalyst may incorporate a binder for preserving and enhancing catalyst integrity. Conventional binders include silica, alumina, titania, silica-titania, and various clays since such conventional materials are well known.

The production of hydrogen peroxide is carried out in a hydrogen peroxide production zone. In the hydrogen peroxide production zone a hydrogen stream and an oxygen containing stream, such as air or oxygen, are employed to directly produce hydrogen peroxide from hydrogen and oxygen as disclosed in U.S. Pat. No. 5,236,692 or to indirectly produce hydrogen peroxide by the well-known cyclic anthraquinone process as described in U.S. Pat. No. 2,935,381. The well-known anthraquinone process involves two successive steps. In a first step, the alkylanthraquinone dissolved in a water immiscible solvent is hydrogenated in the presence of a particulate hydrogenation catalyst, following which the catalyst is removed to yield a second solution of the corresponding alkylanthrahydroquinone in the solvent. The second solution is oxygenated by means of air or oxygen to regenerate the solution of the alkylanthraquinone which is recycled to the first step following the separation of the solution from the formed hydrogen peroxide. The separation is typically carried out by countercurrent extraction with water. The aforementioned U.S. Patents related to the production of hydrogen peroxide are hereby incorporated by reference. The hydrogen peroxide produced by either method is extracted with a water stream to provide an aqueous hydrogen peroxide stream.

DETAILED DESCRIPTION OF THE DRAWINGS

The process of the present invention is hereinafter described with reference to the figures which illustrates various aspects of the process. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation systems, etc. It may also be discerned that the process flow depicted in the figure may be modified in many aspects without departing from the basic overall concept of the invention.

With reference to FIG. 1, a synthesis gas stream is typically derived from a syngas production zone or synthesis gas plant (not shown). At least a portion of a synthesis gas stream 10 is passed via line 12 to a carbon oxide conversion zone 101. An oxygenate product stream comprising methanol and/or dimethyl ether is withdrawn from the carbon oxide conversion zone 101 in line 16. At least a portion of the oxygenate product stream 16 is passed to an olefin production zone 102 to produce a reactor effluent comprising light olefins having from 2 to 4 carbon atoms per molecule and water. The oxygenate product stream 16 is introduced to an olefin production zone 102 containing a fluidized bed of molecular sieve catalyst in the presence of a diluent such as steam or other inert material to produce a reactor effluent stream 18 comprising hydrocarbons, $CO_2$, and water. The hydrocarbons produced in the olefin production zone include ethylene, propylene, and butylenes. The reactor effluent stream 18 is flashed in a water separation zone 116 to remove at least a portion of the water in associated water stream 17 and to provide a first hydrocarbon stream 15. The first hydrocarbon stream 15 is passed to a caustic wash zone 114 wherein the first hydrocarbon stream 15 is contacted with a caustic solution 13 in the conventional manner to remove carbon dioxide and thereby produce a spent caustic stream 19 and an acid reduced hydrocarbon stream 21. The acid reduced hydrocarbon stream 21 is passed via line 21' to a drying zone 112 containing an adsorbent such as zeolite X and, more preferably, containing an adsorbent such as zeolite 13X to produce a light hydrocarbon stream 20 with a water content of less than about 1 ppm-wt. The light hydrocarbon stream 20 is passed to a demethanizing zone 103 to produce a methane stream 23 comprising methane and lighter gases such as hydrogen, carbon monoxide and carbon dioxide, and a $C_2$ plus stream 29. The $C_2$ plus stream 29 is passed to a deethanizer zone 108 via line 27 to produce a $C_2$ minus stream 25 comprising ethane and ethylene and a $C_3$ plus stream 24. The $C_2$ minus stream is passed to an ethylene separation zone 110 to produce a high purity ethylene product stream 22, comprising more than about 98 vol-% ethylene and an ethane stream 22' which may be used for fuel. The $C_3^+$ stream 24 is passed via line 26 to a $C_3/C_4$ fractionation zone 104 wherein the $C_3$ and $C_4$ hydrocarbons are separated into a crude propylene stream in line 28 and a $C_4^+$ stream comprising butenes in line 30. A portion of the crude propylene stream 28 may be withdrawn as a crude propylene product in line 35. Preferably, the crude propylene stream comprises at least about 90 vol-% propylene, more preferably the crude propylene stream comprises more than about 92 vol-% propylene, and most preferably the crude propylene stream comprises from about 95 to about 98 vol-% propylene. Alternately, the separation of propylene may be carried out in a superfractionator, propane-propylene splitter column to produce a 99+vol-% propylene stream, but significant captial and operating cost savings are realized in the scheme of the present invention by the preparation of a crude propylene stream combined with the return of at least a portion of any unreacted propylene to the propylene oxide zone. A portion of the crude propylene stream 28 is passed to a propylene oxide zone 105 to produce a propylene oxide product 32. In the propylene oxide zone 105, an aqueous hydrogen peroxide stream 46 is reacted with the crude propylene stream 28 over a metal-substituted silicate catalyst to produce the propylene oxide product 32, a spent water stream 36 and an unreacted propylene stream 34. The unreacted propylene stream 34 is recycled to the fractionation section of the oxygenate conversion process via lines 34, 48, and 45 to a point where the unreacted propylene stream 45 is admixed with the acid reduced hydrocarbon stream 21. The resulting admixture in line 21' is passed to the drying zone 112 to reduce the moisture content prior to further fractionation. In one alternate embodiment, if the ethylene content of the unreacted propylene stream 34 is less than about 200 ppm, the unreacted propylene stream may be dried in a second dryer (not shown) and passed via lines 34, 47, and 26 to the $C_3/C_4$ fractionation zone 104 whereby the unreacted propylene is recovered and returned to the propylene oxide zone 105. In another embodiment, the unreacted propylene stream may be dried in the second dryer and passed via lines 34, 48, 45' and admixed with the C2 plus stream 29, and the resulting $C_2$ plus admixture is passed to the deethanizer zone 108. At least a portion of the spent water stream 36 depleted in hydrogen peroxide is admixed with a make-up water stream 40 and passed as an admixed water stream in line 42 to a hydrogen peroxide production zone 106. The spent water stream from the epoxidation reaction zone will contain some heavy components such as propylene glycol and propylene glycol ethers including 1-methoxy propylene glycol and 2-methoxy propylene glycol. These heavy components must be removed from the spent water stream prior to returning the spent water to the hydrogen peroxide production zone 106. The removal of the heavy components is addressed in the discussion of FIG. 2 herein below. In the hydrogen peroxide production zone a hydrogen stream 44 and an oxygen-containing stream 49, such as air or oxygen, are employed to directly produce hydrogen peroxide from hydrogen and oxygen or to indirectly produce hydrogen peroxide by the cyclic anthraquinone process. The hydrogen peroxide produced by either method is extracted with the admixed water stream 42 to provide the aqueous hydrogen peroxide stream 46. The hydrogen stream 44 may be derived from any source, but is preferably derived from a slip-stream of the syngas stream 10 which is passed via line 14 to a hydrogen separation zone 107 to separate hydrogen from the carbon oxide and produce a hydrogen stream in line 44 comprising said hydrogen and a waste gas stream 4 comprising said carbon oxide. In separating hydrogen from synthesis gas streams which contain significant amounts of carbon dioxides, the hydrogen separation zone may include a membrane separation zone in combination with an acid gas removal step (not shown). The synthesis gas slip stream is first passed to the membrane separation zone to produce a permeate stream comprising hydrogen and carbon dioxide, and subsequently, the permeate stream is passed to a conventional physical absorption process based on washing the permeate stream with agents such as alcohol, amines, methanol, or carbonates for the removal of carbon dioxide to achieve the desired hydrogen purity. The waste gas stream 4 may be passed to a synthesis gas plant (not shown) or admixed with the syngas stream 12 prior to passing the syngas stream 12 to the carbon oxide conversion zone 101.

The $C_4^+$ stream 30 is withdrawn from the $C_3/C_4$ fractionation zone 104 and may be passed to further separation or conversion facilities to produce alcohols or ethers for petrochemical or fuel use.

Figure 2:
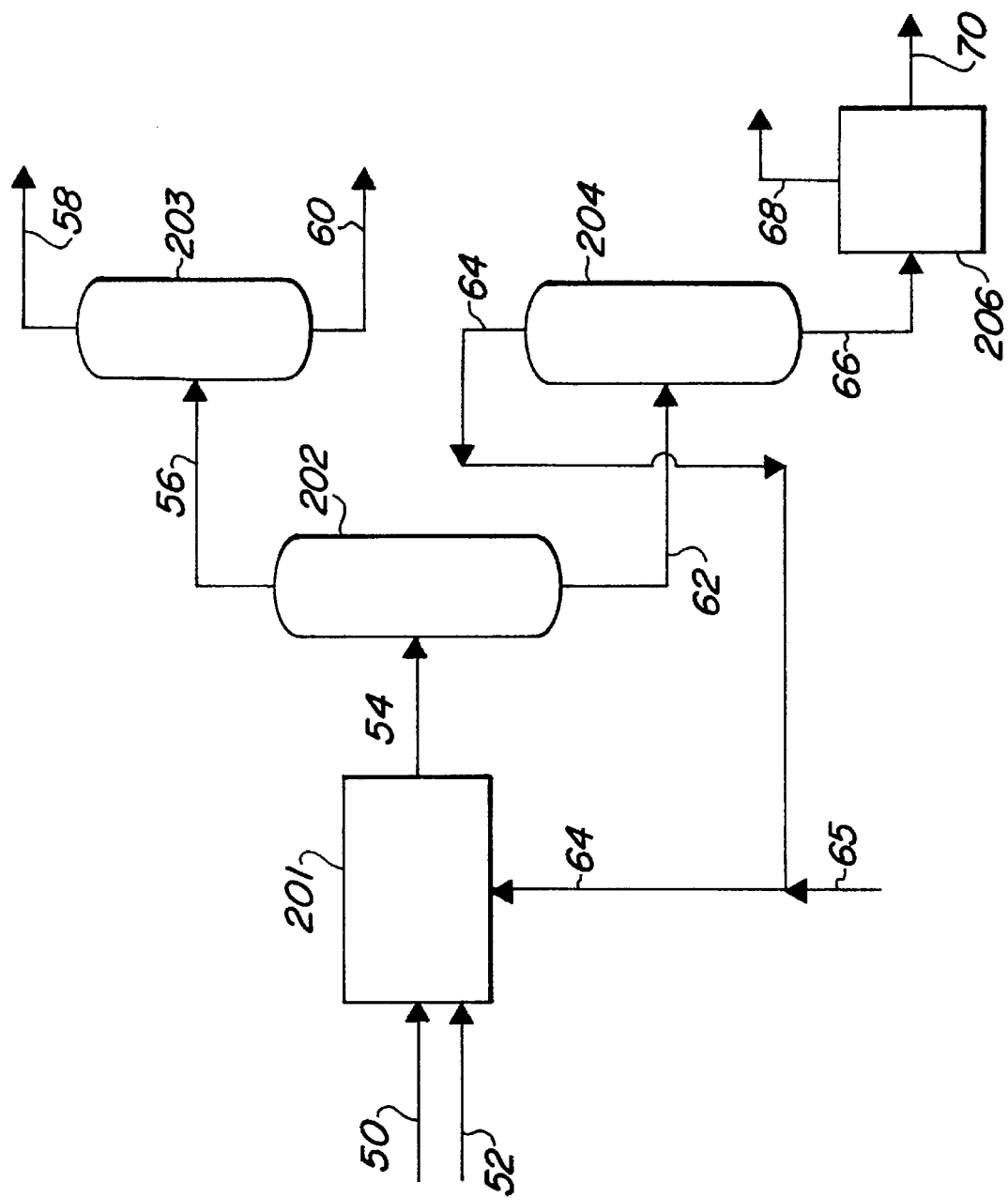
FIG. 2 is a schematic process flow diagram illustrating the epoxidation process section of the present invention.

With reference to FIG. 2, the epoxidation reaction for the production of propylene oxide from hydrogen peroxide and propylene is carried out in an epoxidation reaction zone 201 in the presence of metal-substituted silicate catalyst and in the presence of an a solvent such as an alcohol like methanol. Returning to FIG. 2, The propylene feedstream 50 and the hydrogen peroxide solution 52, along with a solvent stream 64 are passed to the epoxidation reaction zone 201 to produce an epoxidate stream 54. The epoxidate stream 54, or the reactor effluent from the epoxidation reaction zone 201 comprises propylene oxide, light hydrocarbons such as ethane, propane, and unreacted propylene, water, and the solvent. The epoxidate stream 54 may also contain some heavy organic compounds such as propylene glycol and derivatives thereof including 1-methoxy propylene glycol, 2-methoxy propylene glycol, and heavier propylene glycol oligomers. Preferably the epoxidate stream 54 comprises less than about 5 wt-% heavy organic compounds relative to the total amount of propylene oxide produced. The epoxidate stream 54 is passed to a first separation zone 202 wherein a propylene oxide/light ends stream mixture 56 is separated from a solvent/water mixture 62. The propylene oxide/light ends stream 56 is passed to a second separation zone to provide a light ends stream 58 and a propylene oxide product 60. The light ends stream 58 comprises unreacted propylene and is returned to the demethanizer zone in the olefin-production zone which is operated to return the unreacted propylene from the epoxidation reaction zone thereby improving the overall conversion of propylene to propylene oxide.

The solvent/water mixture 62 is fractionated in a third separation zone 204 to produce the solvent stream 64 and a spent water stream 66. In the selection of the solvent, due consideration must be given either to avoid the formation of an azeotrope in this separation, or otherwise to break the resulting azeotropic composition in a conventional manner well-known to those skilled in the art. By way of example, methanol is a preferred solvent that can easily be fractionated from water without the formation of azeotropes. At least a portion of the solvent stream is returned to the epoxidation reaction zone 201. Any portion of the solvent stream 64 which may be withdrawn for disposal or lost in processing may be replaced with a makeup alcohol stream 65 to retain the purity of the solvent stream 64. When methanol is the solvent, preferably, the solvent stream 64 comprises at least 80 wt-% methanol. The spent water stream 66 comprises the heavy organic compounds. The spent water stream 66 is passed to a separation zone 206 such as an evaporator, a distillation zone or a sorption zone. Preferably, such a sorption zone contains a sorbent such as a solid adsorbent selected from the group consisting of silica gel, silicates, activated charcoal, and mixtures thereof to remove and recover—upon desorption—the heavy organic compounds as a heavy organic compound stream 68 and to produce a water stream 70. The heavy organic compound stream has value as a solvent or can be further processed for the recovery of propylene glycol. The water stream 70 has a reduced amount of heavy organic compounds relative to the spent water stream 66 and preferably has a concentration of heavy organic compounds less than about 100 ppm-wt.

The following examples are only used to illustrate the present invention and are not meant to be limiting.

EXAMPLES

Example I

A technical grade propylene stream withdrawn from an olefin production zone of the present invention will comprise propylene in a concentration ranging from about 98 to about 99 mol-% with about 0.05% ethane and the balance consisting essentially of propane. According to the process of the present invention as shown in FIG. 1, a 100 kmole propylene stream is passed to an epoxidation zone and is therein contacted with about a 20% aqueous hydrogen peroxide solution over a titania-supported titanosilicate catalyst at a temperature ranging from about 40°–60° C. and a molar ratio of propylene: hydrogen peroxide of about 1:1. In the epoxidation zone, approximately 95% of the propylene is converted to produce propylene oxide. The hydrogen peroxide is about 95% efficient in the overall conversion to the oxide producing about 93.5 kmole of propylene oxide, a dilute water phase, and a gas purge stream. The overall material balance for the major components is shown in the following table.

|  | FEEDSTOCK | $H_2O_2$ | PROPYLENE OXIDE kmole | WATER PHASE | GAS PURGE |
| --- | --- | --- | --- | --- | --- |
| ETHANE | 0.05 | — | — | — | 0.05 |
| PROPYLENE | 98.50 | — | — | — | 5.00 |
| PROPANE | 1.4 | — | — | — | 1.45 |
| PEROXIDE | — | 98.2 | — | 4.7 | — |

| | FEEDSTOCK | $H_2O_2$ | PROPYLENE OXIDE kmole | WATER PHASE | GAS PURGE |
|---|---|---|---|---|---|
| PROPYLENE OXIDE | — | — | 93.5 | — | — |
| WATER | — | 392.8 | — | 486.3 | — |
| TOTAL | 100.00 | 491.0 | 93.5 | 491.0 | 6.50 |

The gas purge, containing about 77 mol-% propylene is dried in an adsorbent filled dryer and returned to the separation zone of the olefin production zone wherein the dry gas purge is admixed with demethanizer bottoms prior to introducing the demethanizer bottoms to the deethanizer. The deethanizer removes ethane and lighter material to produce a $C_3^+$ stream which is passed to a $C_3$ splitter to produce a technical grade propylene stream comprising about 98.5 mol-% propylene. The technical grade propylene stream is subsequently returned to the epoxidation zone. At least a portion of the water phase, now having a reduced concentration of hydrogen peroxide relative to the hydrogen peroxide solution charged to the epoxidation zone is returned to the hydrogen peroxide production zone as a lean hydrogen peroxide stream. In the hydrogen peroxide production zone, the lean hydrogen peroxide stream of the present invention is contacted with the working solution of an anthraquinone-based process to recover a hydrogen peroxide product comprising from 2 to 35 percent hydrogen peroxide.

EXAMPLE II

The following evaluation was performed in a feed bed continuous, downflow (13 mm I.D.) stainless steel reactor. The reactor walls had been passivated with nitric acid prior to filling the reactor with 10 cc (about 5 grams) of crystalline titanium silicate with 2% titanium in the MFI structure (TS-1) available from National Chemical Laboratory, Pune 411008, India. A propylene stream was admixed with an aqueous hydrogen peroxide/alcohol stream comprising 5 wt-% hydrogen peroxide, 11.6 wt-% water, and 83.4 wt-% methanol and passed to the reactor at a temperature of about 30° C. and a pressure of about 3.6 MPa at a liquid hourly space velocity of about 0.8. The ratio of hydrogen peroxide to propylene in the feed to the reactor was maintained at about 0.9 kmoles/Kmole. A gas chromatographic analysis of the liquid product indicated the presence of heavy compounds such as propylene glycol, 1-methyl propanol, and 2-methyl propanol in a total amounts of heavy compounds ranging from about 500 to about 2500 ppm-wt.

We claim:

1. A process for the production of propylene oxide from a feedstream comprising hydrogen and a carbon oxide, said process comprising:
    a) passing a portion of said feedstream to an oxygenate production zone to produce an oxygenate stream and passing said oxygenated stream to an olefin production zone containing a metal aluminophosphate catalyst to produce a light hydrocarbon stream comprising propylene;
    b) separating a crude propylene stream from said light hydrocarbon stream and passing said crude propylene stream and an aqueous hydrogen peroxide stream to an epoxidation reaction zone containing an epoxidation catalyst to produce a propylene oxide product, a light ends stream comprising unreacted propylene and a spent water stream comprising heavy components;
    c) separating at least a portion of said feedstream in a hydrogen separation zone to provide a hydrogen stream comprising hydrogen and reacting in a peroxide production zone said hydrogen stream and an oxygen-containing stream to produce hydrogen peroxide and removing the hydrogen peroxide with a water stream to produce said aqueous hydrogen peroxide stream; and
    d) treating said spent water stream to remove the heavy components and produce a treated water stream and recycling at least a portion of the treated water stream to provide the water stream.

2. The process of claim 1 wherein said aqueous hydrogen peroxide concentration ranges from 2 to 35 percent.

3. The process of claim 1 wherein said epoxidation catalyst comprises a metal-substituted silicate.

4. The process of claim 3 wherein said metal-substituted silicate contains metal compounds selected from the group consisting of molybdenum, tungsten, chromium, titanium, and mixtures thereof.

5. The process of claim 1 wherein said oxygenate stream is selected from the group consisting of methanol, ethanol, propanol, dimethyl ether, and mixtures thereof.

6. The process of claim 1 wherein said oxygenate stream comprises methanol and dimethyl ether.

7. The process of claim 1 wherein said metal aluminophosphate catalyst is selected from the group consisting of SAPO-17, SAPO-34, SAPO-18, and mixtures thereof.

8. The process of claim 1 wherein said hydrogen separation zone comprises a membrane separation zone or a pressure swing adsorption zone.

9. The process of claim 1 wherein said peroxide production zone comprises the production of hydrogen peroxide by direct oxidation of hydrogen or by the indirect hydrogenation of an alkylanthraquinone and the subsequent oxidation of an alkylanthrahydroquinone.

10. A process for the production of propylene oxide from a syngas stream comprising hydrogen and a carbon oxide, said process comprising the steps of:
    a) passing at least a portion of said syngas stream to an oxygenate production zone to produce an oxygenate stream;
    b) passing the oxygenate stream to an olefin production zone to produce an olefin-containing effluent stream comprising ethylene, propylene and butylene;
    c) passing said effluent stream to a first fractionation zone wherein said ethylene is separated from said effluent stream to provide an ethylene product stream and a $C_3^+$ stream;
    d) passing said $C_3^+$ stream to a second fractionation zone wherein said propylene is separated from said $C_3^+$ stream to provide a propylene stream and a $C_4^+$ stream;
    e) passing said propylene stream to a propylene oxide zone and therein contacting said propylene stream with a hydrogen peroxide stream in the presence of a metal-substituted silicate catalyst and a solvent at epoxidation conditions effective to produce a propylene oxide product, a spent water stream and an unreacted propylene stream;

f) returning at least a portion of said unreacted propylene stream to said first fractionation zone;

g) treating at least a portion of the spent water stream to provide a treated water stream; and, h) passing a portion of said syngas stream to a hydrogen separation zone to produce a hydrogen stream comprising hydrogen and passing said non-permeate stream and said treated water stream to a hydrogen peroxide production zone to provide said hydrogen peroxide stream.

11. The process of claim 10 wherein said solvent comprises methanol.

12. The process of claim 10 wherein said metal-substituted silicate catalyst comprises a titania-supported titanosilicate.

13. The process of claim 10 wherein said hydrogen peroxide stream comprises from about 5 to about 50 weight percent hydrogen peroxide.

14. The process of claim 10 wherein said treating step comprises contacting said portion of the spent water stream in a sorption zone containing a solid adsorbent selected from the group consisting of silica gel, silicates, activated charcoal, and mixtures thereof to remove heavy organic compounds from the water stream.

15. The process of claim 14 wherein said heavy organic compounds comprise propylene glycol and derivatives thereof.

16. The process of claim 10 wherein said spent water stream comprises heavy organic compounds.

17. The process of claim 16 wherein said treated water stream comprises less than about 100 ppm-wt of heavy organic compounds.

18. The process of claim 10 wherein said spent water is treated in an evaporator or a distillation zone to provide said treated water stream.

19. The process of claim 10 wherein the propylene stream comprises at least 90 vol-% propylene.

20. The process of claim 10 wherein the propylene stream comprises from about 95 to about 98% vol-% propylene.

21. The process of claim 10 wherein the epoxidation conditions include an epoxidation temperature ranging from about 0° to about 100° C. and an epoxidation pressure less than about 3.5 MPa.

* * * * *